(12) United States Patent
Arps et al.

(10) Patent No.: US 10,226,419 B2
(45) Date of Patent: Mar. 12, 2019

(54) METHODS FOR MANUFACTURING IMPLANTS

(71) Applicant: ProMed Pharma, LLC, Plymouth, MN (US)

(72) Inventors: James H. Arps, Chanhassen, MN (US); Matthew Petersen, Minneapolis, MN (US)

(73) Assignee: PROMED PHARMA, LLC, Plymouth, MN (US)

( * ) Notice: Subject to any disclaimer, the term of this patent is extended or adjusted under 35 U.S.C. 154(b) by 216 days.

(21) Appl. No.: 14/847,782

(22) Filed: Sep. 8, 2015

(65) Prior Publication Data

US 2016/0067178 A1 Mar. 10, 2016

Related U.S. Application Data

(60) Provisional application No. 62/047,344, filed on Sep. 8, 2014.

(51) Int. Cl.

| | |
|---|---|
| A61K 9/00 | (2006.01) |
| B29C 51/12 | (2006.01) |
| A61K 31/57 | (2006.01) |
| A61K 47/32 | (2006.01) |
| A61K 47/34 | (2017.01) |
| A61K 31/567 | (2006.01) |
| B29K 67/00 | (2006.01) |
| B29L 31/00 | (2006.01) |
| B29K 105/00 | (2006.01) |
| B29C 47/00 | (2006.01) |
| B29C 47/02 | (2006.01) |

(52) U.S. Cl.
CPC .......... *A61K 9/0036* (2013.01); *A61K 31/567* (2013.01); *A61K 31/57* (2013.01); *A61K 47/32* (2013.01); *A61K 47/34* (2013.01); *B29C 51/12* (2013.01); *B29C 47/0011* (2013.01); *B29C 47/028* (2013.01); *B29K 2067/046* (2013.01); *B29K 2105/0035* (2013.01); *B29L 2031/7148* (2013.01); *B29L 2031/754* (2013.01)

(58) Field of Classification Search
CPC .................................................... A61K 9/0036
See application file for complete search history.

(56) References Cited

U.S. PATENT DOCUMENTS 3,926,188 A * 12/1975 Baker .................. A61K 9/0004
424/427
4,758,435 A 7/1988 Schaaf
4,945,132 A 7/1990 Wilkus et al.
5,360,590 A 11/1994 Wheeler
(Continued)

OTHER PUBLICATIONS

Morrow, et al., "Sustained release of proteins from a modified vaginal ring device", European Journal of Pharmaceutics and Biopharmaceutics, 77, 2011, 3-10.

*Primary Examiner* — Benjamin J Packard
(74) *Attorney, Agent, or Firm* — Billion & Armitage; Benjamin C. Armitage

(57) ABSTRACT

Pharmacologically active implants, in particular subcutaneous implants, intrauterine devices, and intravaginal rings, are provided herein. Methods for forming an active ingredient-containing core are described. Methods for laminating an active ingredient-containing core to form a rate-controlling sheath are also described.

12 Claims, 2 Drawing Sheets

(56) References Cited

U.S. PATENT DOCUMENTS

| | | | |
|---|---|---|---|
| 5,662,923 A * | 9/1997 | Roreger | A61K 9/0014 424/445 |
| 5,756,115 A | 5/1998 | Moo-Young et al. | |
| 6,010,715 A | 1/2000 | Wick et al. | |
| 6,264,638 B1 | 7/2001 | Contente | |
| 2013/0302733 A1 | 11/2013 | Chun et al. | |

* cited by examiner

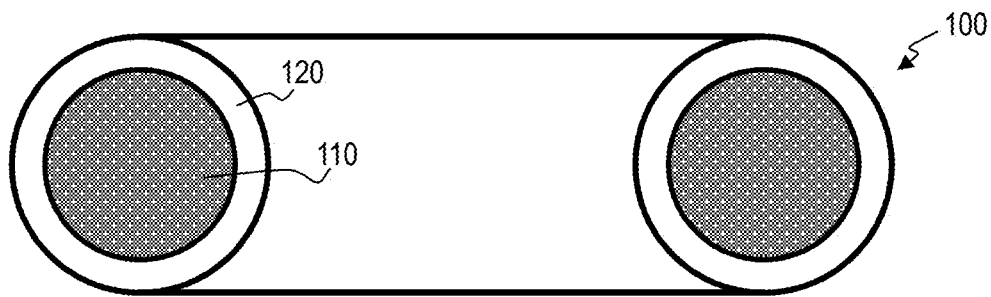
FIG 1
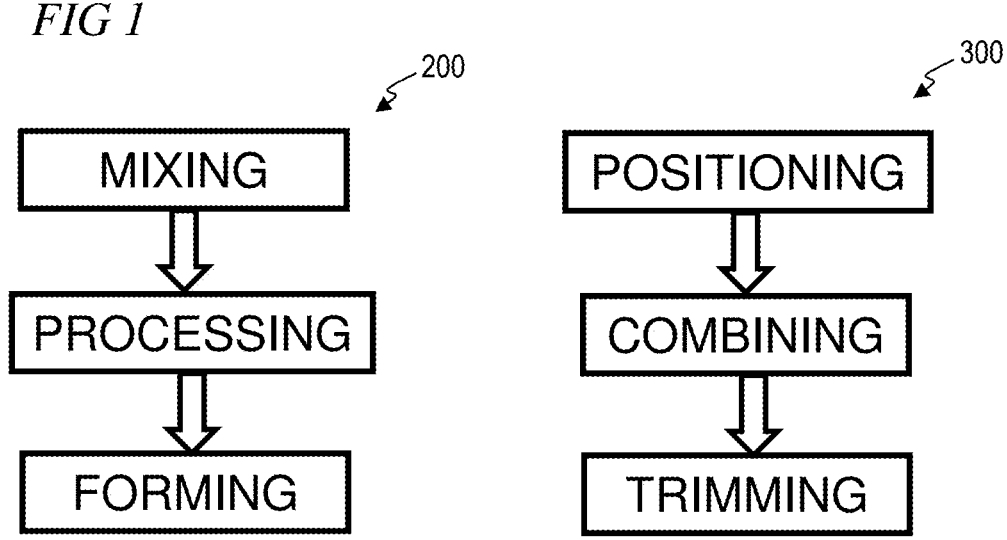
FIG 2
FIG 3A
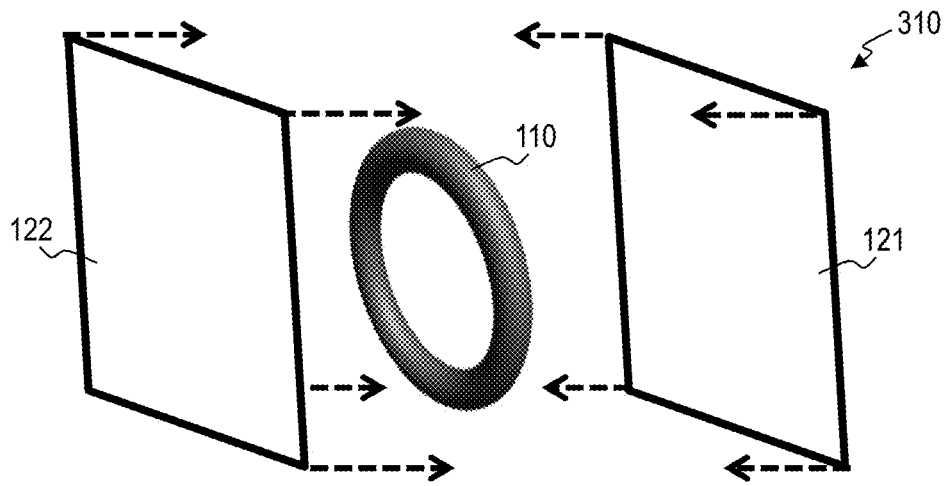
FIG 3B

METHODS FOR MANUFACTURING IMPLANTS

BACKGROUND

This application claims benefit of U.S. Provisional Application No. 62/047,344, filed on Sep. 9, 2014 and which application is incorporated herein by reference. A claim of priority is made.

Solid drug delivery implants are utilized to provide sustained release of an active agent or drug over a period of days, weeks, months, or years as an attractive alternative to more conventional dosage forms, such as oral or parenteral dosages. A few examples of such products include subcutaneous "rod" implants, intrauterine devices, and intravaginal rings (IVRs). In order to provide consistent and constant drug release rates a preferred approach is to embed the drug within a polymer matrix of material and encapsulate it within a polymer membrane or sheath to provide a barrier for controlled drug diffusion and release. Typically the drug is incorporated into the polymer by a hot melt extrusion process to produce drug-doped pellets. These pellets are then extruded to form the drug-filled core, and a rate-controlling sheath is coextruded over the drug-filled core. Drug-filled cores, and appurtenant sheaths, are extruded in lengths, typically with circular cross-sections. When continuous implant shapes are desired, the sheathed cores must be cut to length and the ends must be welded together.

In cases where a very thin (<0.5 mm, frequently 0.10 mm or less) sheath thicknesses are advantageous or required, control of thickness during extrusion can be problematic and required expensive in-line process control and equipment. The extrusion process also subjects the drug to significant thermal loads which can cause a range of deleterious effects, including chemical degradation of the drug and/or matrix and sheath components, crystallization within the polymer matrix. Further, the process often demands relatively large amounts of material resulting in wasted active ingredients and polymer material. Additionally, coextrusion equipment and subsequent process steps (e.g. welding into rings) can also be expensive and engender process inefficiency.

SUMMARY

In general, this disclosure describes techniques for manufacturing active ingredient cores. Techniques further describe methods for laminating active ingredient cores to form a rate-controlling sheath. In particular, this disclosure describes techniques for manufacturing subcutaneous implants, intrauterine devices, and intravaginal rings (IVRs), although it should be noted that the techniques of this disclosure are generally applicable to pharmacologically active implants.

According to an example of the disclosure, a method of forming a pharmacologically active homogenous core matrix mixture comprises combining one or more polymers with one or more active ingredients to form a mixture; and mixing the mixture sufficient to impart heat and until a homogenous mixture is achieved; wherein heat imparted to the mixture is sufficient to melt the polymer without substantially altering the pharmacological properties of the active ingredient.

According to another example of the disclosure, a method of forming a rate-controlling release membrane over a pharmacologically active core comprises positioning a core between two layers film; applying one or more of heat and pressure to the core and film layers such that each film layer mechanically combines with one or more of the ring-shaped core and the opposite membrane film; and trimming excess film to form a sheath having a substantially uniform thickness.

The details of one or more examples are set forth in the accompanying drawings and the description below. Other features, objects, and advantages will be apparent from the description and drawings, and from the claims.

BRIEF DESCRIPTION OF THE DRAWINGS

The accompanying drawings illustrate non-limiting example embodiments of the invention.

FIG. 1 illustrates a cross sectional side view of a ring-shaped implant, according to one or more embodiments of this disclosure.

FIG. 2 illustrates a method for forming an inner core, according to one or more embodiments of this disclosure.

FIG. 3A illustrates a method for laminating an inner core, according to one or more embodiments of this disclosure.

FIG. 3B illustrates a perspective view of an inner core being positioned between sheath materials, according to one or more embodiments of this disclosure.

DETAILED DESCRIPTION

Figure 3C:
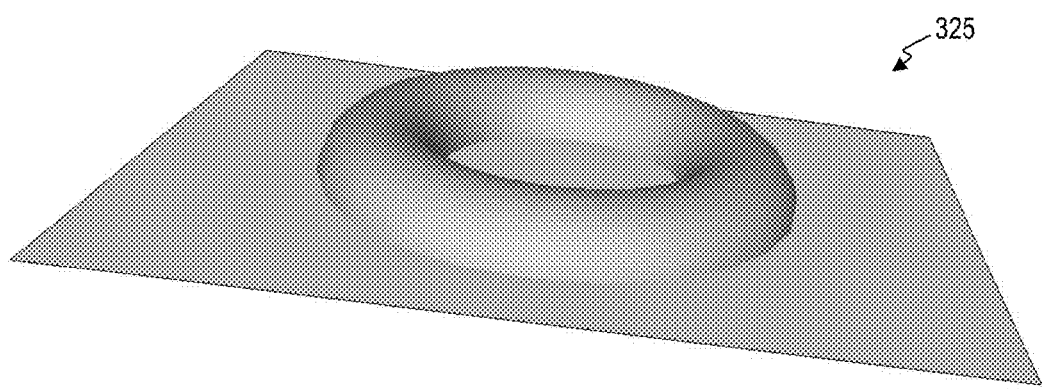
FIG. 3C illustrates a perspective view of a post-combining product, according to one or more embodiments of this disclosure.

The present invention is described with reference to the attached figures, wherein like reference numerals are used throughout the figures to designate similar or equivalent elements. The figures are not drawn to scale and they are provided merely to illustrate the invention. Several aspects of the invention are described below with reference to example applications for illustration. It should be understood that numerous specific details, relationships, and methods are set forth to provide an understanding of the invention. One skilled in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

This disclosure provides novel solid drug delivery implants and methods of manufacture therefor. As used herein, "implants" can refer to an object which contacts the body of an animal or human, or an object which is positioned within an organ or an orifice. For example, an implant can be positioned within a mouth, within a vagina, underneath an epidermis, or within a uterus. Examples of bodily positions are non-limiting; embodiments provided herein can be utilized throughout a body as necessary or advantageous. Implants can include subcutaneous implants, intrauterine devices, and intravaginal rings (IVRs).

FIG. 1 illustrates a cross-sectional side view of an implant 100, comprising an inner core 110 and a rate-controlling sheath 120. Inner core 110 can comprise one or more polymer excipients and at least one active ingredient. The polymer fraction forms a matrix throughout which the one or more active ingredients are dispersed. In many embodiments, the active ingredient is substantially uniformly dispersed, such as having a material uniformity less than +/−5%, less than +/−4%, less than +/−3%, less than +/−2%, or less than +/−1%. Polymers can include thermoplastics such as thermoplastic urethanes, polyethylene terephthalate polyesters, silicone thermoplastics, LTV silicone elastomers, and polyamides. Specific examples of polymers can include polyoxymethylene, thermoplastic copolyester elastomer (TPC-ET), polyethylene homopolymer, poly(vinyl acetate) homopolymer, poly(lactic acid) homopolymer, poly(caprolactone), polypropylene, poly(ethylene oxide), poly(styrene), poly(vinyl chloride) poly lactic-co-glycolic acid, and ethylene vinyl acetate (EVA). EVA comprises ethylene and vinyl acetate, with a weight percent (wt. %) of vinyl acetate ranging from about 5 wt. % to about 40 wt. %, about 7 wt. % to about 34 wt. %, or about 9 wt. % to about 28 wt. %.

Active ingredients can include any pharmacologically active agents, such as contraceptive hormones. Contraceptive hormones can include estradiol, ethinyl estradiol, etonogestrel, progesterone, ethisterone, norethisterone acetate, norethynodrel, levonorgestrel, or gestodene, although others are similarly suitable as would be recognized by one of skill in the art after review of this disclosure. Inner core 110 can further comprise opacifiers, such as barium sulfate, or dyes.

Inner core 110 can have a cross-sectional shape which is circular, or polygonal. In some embodiments, a cross-sectional shape is chosen to accommodate manufacturing processes or equipment. The overall shape of the inner core 110 can be tubular or rod shaped, or a continuous shape. A continuous shape can include a circle, oval, triangle, square, or other polygons. Shapes can include a mixture of straight and curved edges, such as a semi-circle. Shapes can include irregular geometries which can be in some embodiments designed to match the contour of an implant positioning location within a body.

Rate-controlling sheath 120 can comprise one or more polymers, such as those suitable for the inner core 110. Rate-controlling sheath 120 can comprise a similar composition to the polymer fraction of the inner core 110. In some embodiments, rate-controlling sheath 120 and inner core 110 share at least one common polymer component. Composition of the rate-controlling sheath can be determined based on permeability of one or more active ingredients. In some embodiments, the compositions of the rate-controlling sheath 120 is selected such that the rate controlling-sheath 120 can melt. Accordingly, in some embodiments, polymers such as silicone are not suitable for the rate-controlling sheath 120. In some embodiments, the rate-controlling sheath has a thickness of between about 1 mil to about 25 mils (about 0.0254 mm to about 0.635 mm).

As shown in FIG. 2, a method 200 of forming an inner core can comprise low-heat mixing 210 inner core components to form a mixture, processing 220 the mixture after mixing, and forming the inner core 230. Inner core components can be supplied for mixing in powdered, pelleted, or liquid forms. One or more objectives of mixing 210 include removing air bubbles from the mixture, homogenizing the mixture to achieve suitable uniformity, elevating the temperature of the mixture above a melting point of at least one polymer. "Melting point" as used herein can refer to a melting point or a glass transition temperature. Homogenizing the mixture includes evenly dispersing the one or more active ingredients throughout the mixture. Mixing 210 can be accomplished via asymmetric mixing, wherein friction of mixing imparts heat on the mixture such that at least one polymer exceeds its melting point.

Asymmetric mixing advantageously imparts sufficient heat onto the mixture, while the heat of the mixture remains below a damaging heat threshold. Active ingredients, such as estradiol, can be heat sensitive, and appreciable chemical degradation of an active ingredient can define a damaging heat threshold. Asymmetric mixing is contactless, and relies on the movement of the vessel to initiate rapid spinning and shearing of a mixture contained within a vessel. As used herein, "contactless" describes the relationship between a mixture and a mixer wherein the only component contacting the mixture is the vessel. This is in contrast to other mixing methods, which use paddles, screws, or other mixing elements to which contact and mix a mixture. Asymmetric mixing can include dual asymmetric mixing. Speed and duration of mixing is controlled to achieve mixing objectives.

An advantage of this approach is that a range of mix sizes is easily attainable by choosing the appropriate mix vessel for the mix size and cleaning can be minimized or eliminated entirely due to minimal contact surfaces. In some cases the heat and shear loads on fragile polymers or active ingredients can be reduced relative to other methods due to the rapid mixing. Vessels can be composed of a range of materials, including polypropylene, thermoplastic polyurethanes, glass, metals such as stainless steel or aluminum, polyethylene, polytetrafluoroethylene, or other suitable container materials. The vessel can comprise a number of materials which are disposable or reusable. Dual planetary mixers can be used. Examples of mixers include FlackTek SpeedMixers™ and Thinky mixers.

Processing 220 can include allowing the mixture to cool under ambient conditions, or cooling the mixture using refrigerants, liquid nitrogen, or the like. Processing 220 can further comprise forming the cooled mixture into powders, granules, pellets, or pieces. An objective of processing 220 is to achieve a particle size which is suitable for forming 230 the inner core. In some embodiments a suitable particle diameter is less than 3 inches, less than 2 inches, or less than 1 inch. Forming the inner core 230 can comprise injection molding, although other methods can be suitable. An objective of forming the inner core 230 includes remaining below a damaging heat threshold.

As shown in FIG. 3A, a method 300 of laminating an inner core can comprise positioning 310 an inner core between two surfaces of rate-controlling sheath material, combining 320 the inner core and sheath material, and trimming 330 excess sheath material. FIG. 3B shows an inner core 110 being positioned 310 between sheath materials 121 and 122. Sheath materials, such as 121 and 122, can be supplied in films with varying thicknesses. In some embodiments, sheath materials comprise a single sheet (not picture) which is folded about an inner core 110. Combining 320 the inner core and sheath material can comprise thermal and/or pressure lamination.

The use of lamination to create dosage forms for pharmaceuticals is novel in the industry, as coextrusion has been the manufacturing method of choice due to familiarity of the technology. In instances where lamination has been employed, the same has been used solely to affect surfaces properties (e.g., wear, resistance, feel, etc.) of products. Lamination can be preferable to coextrusion as it is time efficient, heat and material efficient, and allows for superior operating temperature management and control and uniformity of sheath thickness. Controlling sheath uniformity and thickness is critical as it directly impacts drug release rates and overall implant efficacy and safety. Lamination additionally allows for thinner sheaths to be manufactured, increasing functionality of implants (e.g., drug release rates and use duration). Further, lamination encapsulates an inner core ring as a whole, rather than utilizing a welded joint which can affect drug release rate.

Lamination according to method 300 can be conducted at high pressures, such as at 15 to 20 tons of force. Temperature can include temperatures above the film material's melting point. For example, when EVA is a film component, temperatures of 100-120C can be used. In many embodiments, an operating temperature exceeds the melting point of one or more polymers by less than about 1% of the melting point temperature, less than about 2.5% of the melting point temperature, less than about 5% of the melting point temperature, or less than about 10% of the melting point temperature. When one or more films contain multiple polymer components, a temperature can be chosen to exceed the melting point of one polymer component, of a plurality of polymer components, or all polymer components. A temperature can also be chosen such that the melting point of a core component is not exceeded. When a temperature is used which exceeds the melting point of a core component, lamination process time and/or compressing pressure can be chosen to complement the process temperature in order to avoid chemical degradation and/or physical deformation of the core. Films can combine by one or more of adhering to the opposite film, or adhering to the inner core 110.

Figure 3D:
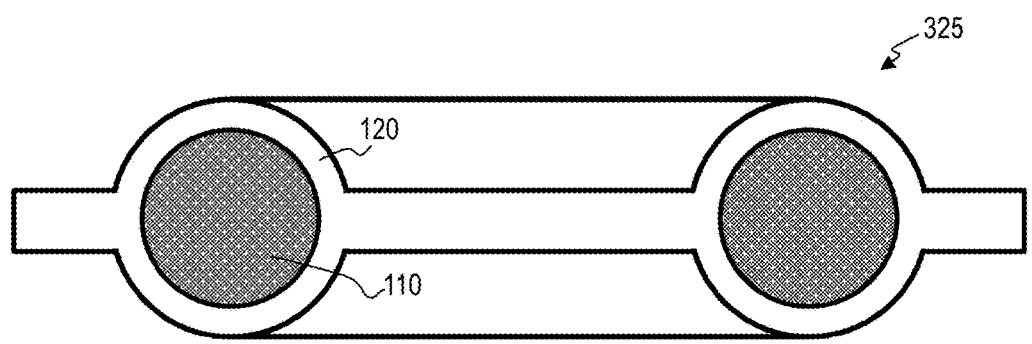
FIG. 3D illustrates a cross-sectional view of a post-combining product, according to one or more embodiments of this disclosure.
Figure 3E:
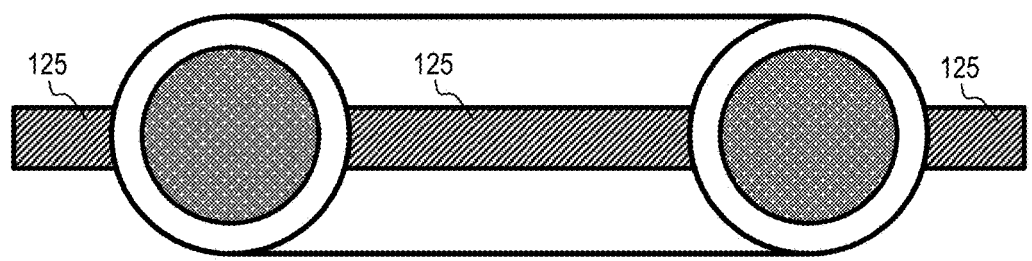
FIG. 3E illustrates a cross-sectional view of a post-combining product with excess material identified, according to one or more embodiments of this disclosure.

FIG. 3C illustrates a post combining 320 product 325. FIG. 3D illustrates a cross-sectional view of a post-combing 320 product 325 which comprises an inner core 110 and a rate-controlling sheath 120. FIG. 3E illustrates a cross-sectional view of a post-combining 320 product 325, wherein excess sheath material 125 is identified. Excess material 125 can be defined as material not substantially contributing to an extrapolated contour of the core. Excess material can also be defined as material which does not provide a consistent sheath thickness. Trimming 330 excess sheath material can be accomplished using a die cutting system, or other suitable means.

EXAMPLE

Manufacture of Prototype Vaginal Ring For Contraception

Approximately 50 g of ethylene vinyl acetate (28% vinyl acetate content) polymer (pellets or granules) was measured into a 150 mL cylindrical container after which 50-250 mg of sex hormones such as ethinyl estradiol and/or etonorgestrel powder or opacifier such as barium sulfate were added. The container was placed in a dual asymmetric mixer (Flaktek SpeedMixer) and mixed for 2-10 minutes at up to 3000 RPM. Upon removal the EVA had melted (estimated temperature 100-120° C.) and the drug was uniformly dispersed throughout the melt. Drug content analysis performed using inductively coupled plasma—optical emission spectroscopy revealed that material uniformity was approximately +/−2%.

After the melt was allowed to cool, the material was processed into granular materials suitable for injection molding by cooling the polymer and processing using with an IKA bladed mill. When EVA was used, the polymer was cooled using liquid nitrogen before and/or during milling. Following milling, particle size was generally less than 0.75 in diameter, though many smaller particles were present.

After milling, this ground material was transferred to an injection molding press and vaginal ring cores with an outer diameter of ~55 mm and a cross section diameter of ~5 mm were molded at approximately 175° C. and at ~5 tons of pressure. The mold was held at ~60° C. during the molding operation and was further cooled 30-40° C. with or without a chiller after injection over ~5 minutes prior to removal of the ring. The ring was then placed between two sheets of EVA film (4-5 mils thick, 9% vinyl acetate content), placed in a mold and compressed at 15-20 tons of force at temperatures sufficient to adhere the laminating layers to one another and the core ring (generally at 100-120° C. for EVA). Excess material was cut and trimmed, leaving a core-sheath ring.

The photographs below shows the overall ring prior to trimming as well as a cross section showing the distinct core and sheath domains. The cutting and trimming operating is ultimately expected to be carried out using an automated die cutting system. Much larger batches of material (up to 5 kg) can be mixed at a time using scaled up dual asymmetric planetary mixing equipment and different geometries are accessible using appropriate molds (for example, rod-shaped) and the same fundamental molding and lamination process. Additionally, it is anticipated that the same process should also be applicable to other thermoplastic elastomers, particularly thermoplastic polyurethanes.

What is claimed is:

1. A method of forming a rate-controlling release membrane over a pharmacologically active ring-shaped core, the method comprising:
    positioning the ring-shaped core between two layers of film;
    applying one or more of heat and pressure to the core and film layers such that each film layer mechanically combines with one or more of the ring-shaped core and the other film layer; and
    trimming excess film to form a sheath having a substantially uniform thickness.

2. The method of claim 1, wherein the ring-shaped core has a continuous shape.

3. The method of claim 1, wherein the ring-shaped core comprises at least one polymer and at least one active ingredient.

4. The method of claim 3, wherein the ring-shaped core further comprises one or more of an opacifier or a dye.

5. The method of claim 3, wherein the one or more polymers comprise one or more of poly lactic-co-glycolic acid and ethylene vinyl acetate.

6. The method of claim 5, wherein the ethylene vinyl acetate comprises about 10 wt. % to about 40 wt. % vinyl acetate.

7. The method of claim 3, wherein the active ingredient comprises a contraceptive hormone.

8. The method of claim 3, wherein the active ingredient comprises one or more of estradiol, ethinyl estradiol, etonogestrel, progesterone, ethisterone, norethisterone acetate, norethynodrel, levonorgestrel, or gestodene.

9. The method of claim 3, wherein the film layers have a thickness of about 1 mil to about 25 mils.

10. The method of claim 1, wherein the film layers comprise one or more of poly lactic-co-glycolic acid and ethylene vinyl acetate.

11. The method of claim 1, wherein applying one or more of heat and pressure to the core and film layers comprises applying pressure between about 15 to about 20 tons of force.

12. The method of claim 1, wherein heat is applied at a temperature that exceeds the melting point of one or more polymers by about 10%.

\* \* \* \* \*